United States Patent [19]

Maupetit et al.

[11] 4,000,202
[45] Dec. 28, 1976

[54] TRICYCLIC NORSESQUITERPENEOLS

[75] Inventors: Pierre Maupetit; Paul José Teisseire, both of Grasse, France

[73] Assignee: Societe Anonyme Roure Bertrand Dupont, Paris, France

[22] Filed: Feb. 21, 1974

[21] Appl. No.: 444,684

[30] Foreign Application Priority Data

Feb. 28, 1973 Switzerland ............... 2884/73
July 3, 1973 Switzerland ............... 9723/73

[52] U.S. Cl. ............... 260/617 F; 260/348 C; 260/586 F; 252/522
[51] Int. Cl.$^2$ ............... C07C 35/22
[58] Field of Search ............... 260/617 F, 348 L

[56] References Cited

OTHER PUBLICATIONS

Buchi et al., J.A.C.S., vol. 86, pp. 4438–4444 (1964).
Teisseire et al., "Chem. Abstracts", vol. 78, Abst. No. 133643u (1973) Abstract of Applicants Ger. Offen., 2,242,913, 3/8/73.

*Primary Examiner*—Donald G. Daus
*Assistant Examiner*—D. B. Springer
*Attorney, Agent, or Firm*—Wallenstein, Spangenberg, Hattis & Strampel

[57] ABSTRACT

Odoriferous agents in the form of certain novel tricyclic norsesquiterpene derivatives are disclosed. These norsesquiterpenes have the formula

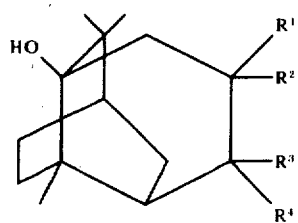

wherein either (a) $R^1$–$R^4$ represent hydrogen or two of the symbols $R^1$ to $R^4$ represent hydrogen and the other two taken together represent oxygen or (b) three of the symbols $R^1$ to $R^4$ represent hydrogen and the fourth represents hydroxy.

Processes for the production of said norsesquiterpene derivatives are also disclosed.

4 Claims, No Drawings

TRICYCLIC NORSESQUITERPENEOLS

DETAILED DESCRIPTION OF THE INVENTION

The invention is concerned with norsesquiterpene derivatives having the general formula

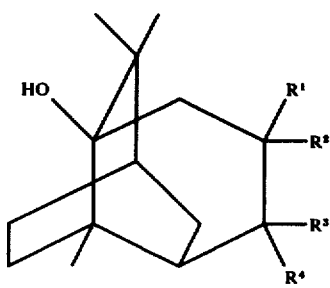

wherein either (a) $R^1$–$R^4$ represent hydrogen or two of the symbols $R^1$ to $R^4$ represent hydrogen and the other two taken together represent oxygen or (b) three of the symbols $R^1$ to $R^4$ represent hydrogen and the fourth represents hydroxy.

The formula I thus includes, for example, the compounds III to VIII shown in the reaction scheme set out herein, that is the epoxy alcohol III, the two glycols IV and VI the two ketoalcohols V and VI, and the alcohol VIII.

The compounds in accordance with the invention of the formula I are useful as odorants and/or as intermediates for the manufacture of such. They also possess fixative properties. Their odour may be described as being camphorous, musty and woody, the odour of the glycols being weaker than that of the other compounds of the formula I. They can be combined in a manner known per se with other odorants to give odorant compositions (for example perfume bases), whereby the content in such compositions may vary within wide limits, for example between about 1 and 20 wt.%. Odorant compositions with a content of one or more of the compounds of the formula I can be used as perfumes or for the perfuming of cosmetic products (soaps, toilet waters, creams etc) as well as for example cleaning agents (detergents, washing agents etc).

The compounds of the formula I can as is set out in the following reaction scheme be prepared by a. subjecting the unsaturated tricyclic alcohol norpatchoulenol (nordehydropatchoulol) of the formula II to epoxidation for the preparation of an epoxy alcohol of the formula III,
b. reducing an epoxy alcohol of the formula III for the preparation of a glycol of the formula IV,
c. oxidising a glycol of the formula IV for the preparation of a ketoalcohol of the formula V,
d. subjecting the unsaturated alcohol norpatchoulenol of the formula II to hydroboration and oxidation for the preparation of a glycol of the formula VI,
e. oxidising a glycol of the formula VI for the preparation of a ketoalcohol of the formula VII,
f. hydrogenating nordehydropatchoulol for the preparation of the alcohol of formula VIII.

Reaction scheme

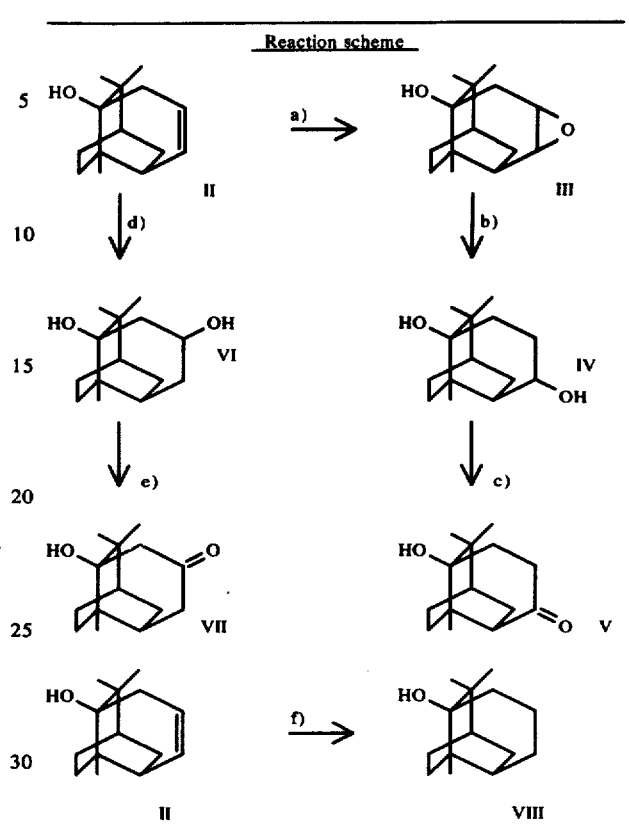

The processes followed in accordance with the invention for the preparation of compounds of formula III to VIII are generally speaking conventional processes. The unsaturated tricyclic alcohol (nordehydropatchoulol or norpatchoulenol) serving as the starting material for the manufacture of the epoxy alcohol III and the glycol VI, is present in natural patchouli oil and can be isolated therefrom according to conventional methods (c.f. French Pat. No. 7,131,577).

The epoxidation of norpatchoulenol II according to reaction (a) can be carried out in a conventional manner using a peracid such as perphthalic acid, perbenzoic acid or peracetic acid. The latter is preferred because of its ready availability.

The reduction of the epoxyalcohol III to the glycol IV according to reaction (b) can likewise be carried out in a conventional manner using a metal hydride such as, for example, diisobutylaluminum hydride.

For the selective oxidation of the glycol IV to the ketoalcohol V according to reaction (c) a chromium trioxide/pyridine complex may be used as the oxidising agent.

For the preparation of the glycol VI from norpatchoulenol II according to reaction (d), the latter is subjected to hydroboration and oxidation in a conventional manner. In the course of this reaction, certain amounts of the isomeric glycol IV also result.

The ketoalcohol VII may be prepared according to reaction (e) from the glycol VI by selective oxidation, for example, according to the 2-phase process of Brown et. al. (J.A.C.S. 83 (1961), 2952) using chromic acid.

The alcohol of formula VIII may be prepared from norpatchoulenol by hydrogenation.

EXAMPLE 1

1 g (4.8 mmol) of norpatchoulenol, dissolved in 50 ml of methylene chloride, and 1 g of dry sodium acetate are added to a 500 ml flask. The thus obtained suspension is stirred vigorously, cooled and then mixed with 15 ml of 35% peracetic acid. The mixture is then left for 48 hours at room temperature, until the norpatchoulenol has practically disappeared. After the addition of 300 ml of water, the reaction mass is extracted with methylene chloride. Then the organic extracts are washed with 9% sodium bicarbonate solution, 10% sodium sulphite solution and finally to neutrality with water. The solvent is then distilled off. There are thus obtained 1.05 g of crystallised, crude epoxyalcohol of the formula III. The substance can be obtained analytically pure (90% yield) by chromatography on silica gel and vacuum sublimation and then shows the following constants:

$[\alpha]_D^{25}(CHCl_3) = + 29.7°$

Mass Spectrum: $C_{14}H_{22}O_2$ (M = 222); 222(M); 207 (M—$CH_3$); 204 (M—$H_2O$); 189 (M—$H_2O$—$CH_3$); 179 (M—$C_3H_7$); 166; 161 (M—$H_2O$—$C_3H_7$); 138; 95; 84

IR-Spectrum: $\nu_{max}^{KBr}(cm^{-1})$: 3520; 3620; 3460; 3000; 1465; 1380-1365; 1305; 1060-1040; 1030; 980; 950-870-810; 755; 740

NMR-Spectrum: (in δ units) 0.89; 1.01; 1.11; 2.80; 3.01.

EXAMPLE 2

100 ml of anhydrous petroleum ether and 10 ml of diisobutylaluminum hydride are added to a 500 ml flask provided with stirrer, reflux condenser and dropping funnel. The reaction medium is kept under a dry nitrogen atmosphere. Then 0.82 g (3.7 mmol) of the epoxyalcohol of formula III obtained according to Example 1, dissolved in 30 ml of dry petroleum ether, are added at ambient temperature to the hydride solution. After this addition, the reaction mixture is held under reflux for 3 hours, then cooled to approximately 0° C, slowly mixed with 20 ml of absolute ethyl alcohol and finally with 250 ml of saturated sodium chloride solution. The reaction mixture is extracted with petroleum ether, whereupon the organic extracts are washed to neutrality with water. Distillation of the solution produces 0.85 g of glycol of formula IV. By chromatography on silica gel, there are obtained 0.80 g of white crystalline product (ca. 82% yield) with the following constants:

Mass Spectrum: $C_{14}H_{24}O_2$ (M = 224); 224 (M); 209 (M—$CH_3$); 206 (M—$H_2O$); 191 (M—$H_2O$—$CH_3$); 188 (M—2 $H_2O$); 181 (M—$C_3H_7$); 173 (M—2 $H_2O$—$CH_3$); 163 (206—$C_3H_7$); 149 (163—$CH_3$); 145 (163—$H_2O$).

IR-Spectrum: $\gamma_{max}^{KBr}$ (cm$^{-1}$): 3420; 3000; 1465; 1380-1360; 1215; 1055; 985; 935; 905.

NMR-Spectrum: (in units) around 1.10; 3.80.

EXAMPLE 3

0.64 (2.86 mmol) of the glycol of formula IV obtained according to Example 2 are dissolved in 100 ml of methylene chloride. After the addition of 12 g of $CrO_3$/pyridine complex, the mixture is stirred for 5 hours at 20°–25° C, then filtered and the filtrate taken up in ethyl ether. The solution is washed with 10% hydrochloric acid to eliminate the pyridine, with 9% bicarbonate solution and finally until neutral with water. After distillation of the solvent, there are obtained 0.60 g of red, crystallised ketoalcohol of formula V, which is purified by chromatography over silica gel. Yield 0.53 g (ca. 85%). The pure product has the following constants:

Mass Spectrum: $C_{14}H_{22}O_2$ (M = 222): 222 (M); 207 (M—$CH_3$); 2204 (M—$H_2O$); 194,189; 179 (M—$C_3H_7$).

IR-Spectrum: $\nu_{max}^{KBr}$ (cm$^{-1}$): 3460; 1700; 1420; 1385-1360; 1255; 1190; 1060-1045; 970; 775.

NMR-Spectrum: (in δ units) 0.83; 1.18 and 1.24 centred at 2.79.

EXAMPLE 4

100 mg (0.48 mmol) of norpatchoulenol of formula I are dissolved in 100 ml of anhydrous tetrahydrofuran in a 50 ml flask. After cooling to 0° C, 3.5 ml of a solution of diborane in tetrahydrofuran are added in one portion thereto. The reaction mixture is then left to warm up to room temperature and left for 24 hours at this temperature. The organoborane formed is directly oxidised. For this purpose, 10 ml of an aqueous 3 N soda solution and 10 ml of 30% $H_2O_2$ are added thereto. The mixture is then stirred for 2 hours at normal temperature and then taken up in saturated sodium chloride solution. After extraction with ether and washing to neutrality, the solution is dried and the ether distilled off. There are thus obtained 100 mg of a crude mixture of the two glycols of formulae IV and VI in the form of a viscous, yellow product. This product is chromatographed through a column of 20 g of silica gel, which enables the separation of the two glycols IV and VI. The glycol VI forms the main product of the reaction. Its constants are the following:

IR-Spectrum: $\nu_{max}$: 3460; 1390; 1360; 1075; 1025; 975; 960; 940 cm$^{-1}$

NMR-Spectrum: (p.p.m.); 0.73; 1.07; 1.20 and 4.20.

EXAMPLE 5

23 mg (0.1 mmol) of the glycol of formula VI obtained according to Example 4 are dissolved in 5 ml of ether, stirred and then 0.5 ml of Brown's solution (J.A.C.S. 83 (1961), 2952) are added thereto at room temperature. The stirring is maintained for 18 hours. The mass is then taken up in water and extracted with ether. The ethereal solutions are washed to neutrality and the ether is distilled off. There is thus obtained crystallised ketoalcohol of formula VII, which is chromatographed over 5 g of silica gel and sublimed under a pressure of 0.5 mm Hg. Yield: 20 mg of white crystals (ca. 80%).

IR-Spectrum: $\nu_{max}$ : 3626; 3525; 1695; 1420–1410; 1380-1360; 1075-1055; 1460; 1278; 1240; 1182; 1028; 970.

We claim:

1. Norsesquiterpene derivatives of the formula

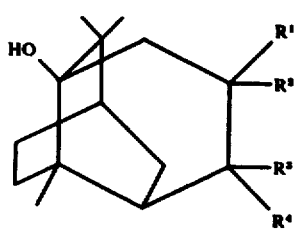
wherein either (a) R$^1$–R$^4$ represent hydrogen or (b) three of the symbols R$^1$ to R$^4$ represent hydrogen and the fourth represent hydroxy.
2. A norsesquiterpene derivative according to claim 1 of formula
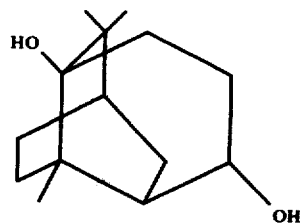
3. A norsesquiterpene derivative according to claim 1 of formula
4. A norsesquiterpene derivative according to claim 1 of formula
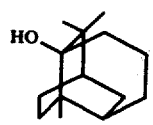
* * * * *